(12) United States Patent
Scherrer et al.

(10) Patent No.: US 12,611,242 B2
(45) Date of Patent: *Apr. 28, 2026

(54) SCREW EXTRACTION SHAFT

(71) Applicant: DEPUY SYNTHES PRODUCTS, INC., Raynham, MA (US)

(72) Inventors: Simon Scherrer, Zurich (CH); Mario Wyss, Egerkingen (CH); Gregor Spreiter, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 368 days.

This patent is subject to a terminal disclaimer.

(21) Appl. No.: 17/660,527

(22) Filed: Apr. 25, 2022

(65) Prior Publication Data

US 2022/0240995 A1 Aug. 4, 2022

Related U.S. Application Data

(63) Continuation of application No. 16/702,251, filed on Dec. 3, 2019, now Pat. No. 11,426,225.

(51) Int. Cl.
| | |
|---|---|
| *A61B 17/88* | (2006.01) |
| *A61B 17/16* | (2006.01) |
| *A61B 17/86* | (2006.01) |
| *A61B 17/92* | (2006.01) |

(52) U.S. Cl.
CPC ...... *A61B 17/8872* (2013.01); *A61B 17/8615* (2013.01); *A61B 17/888* (2013.01); *A61B 17/921* (2013.01)

(58) Field of Classification Search
CPC ............ A61B 17/8872; A61B 17/8615; A61B 17/888; A61B 17/92; A61B 17/8877; A61B 17/8888; B25B 27/18
See application file for complete search history.

(56) References Cited

U.S. PATENT DOCUMENTS

| | | | | |
|---|---|---|---|---|
| 1,547,944 | A | | 7/1925 | Murphree |
| 2,815,054 | A | | 12/1957 | Cummaro |
| 3,216,292 | A | * | 11/1965 | Flegal ..................... B25B 27/18 |
| | | | | 81/53.2 |
| 5,207,132 | A | * | 5/1993 | Goss ..................... B25B 15/005 |
| | | | | 81/460 |

(Continued)

FOREIGN PATENT DOCUMENTS

| | | |
|---|---|---|
| EP | 1 929 975 A1 | 6/2008 |
| EP | 2 932 929 A1 | 10/2015 |
| WO | 2018/154225 | 8/2018 |

OTHER PUBLICATIONS

U.S. Appl. No. 10/076,373, filed Sep. 18, 2018, Strnad et al.

*Primary Examiner* — Tracy L Kamikawa
(74) *Attorney, Agent, or Firm* — Fay Kaplun & Marcin, LLP

(57) ABSTRACT

A bone screw extraction device includes a shaft extending longitudinally from a proximal end to a distal tip, a distal portion of the shaft including a tissue-receiving cavity extending proximally thereinto from the distal tip, the distal tip including a plurality of fingers configured to be received within a driving recess of a bone screw and a plurality of channels extending longitudinally along an exterior surface of the distal portion, each of the plurality of channels extending between adjacent ones of the plurality of fingers.

9 Claims, 5 Drawing Sheets

(56) References Cited

U.S. PATENT DOCUMENTS

| | | | |
|---|---|---|---|
| 6,016,727 A | 1/2000 | Morgan | |
| 6,367,358 B1 * | 4/2002 | Stacy | B25B 15/005 |
| | | | 81/436 |
| 7,225,710 B2 * | 6/2007 | Pacheco, Jr. | B25B 15/005 |
| | | | 81/436 |
| 8,540,756 B2 | 9/2013 | Olsen et al. | |
| 9,261,127 B2 * | 2/2016 | Buhl | B23G 9/002 |
| 11,426,225 B2 * | 8/2022 | Scherrer | A61B 17/8615 |
| 2003/0158555 A1 | 8/2003 | Sanders et al. | |
| 2017/0112555 A1 | 4/2017 | Wallenstein et al. | |
| 2018/0347612 A1 * | 12/2018 | Falkenstein | B25B 15/005 |
| 2019/0254729 A1 * | 8/2019 | Rohlfing | A61B 17/8891 |

* cited by examiner

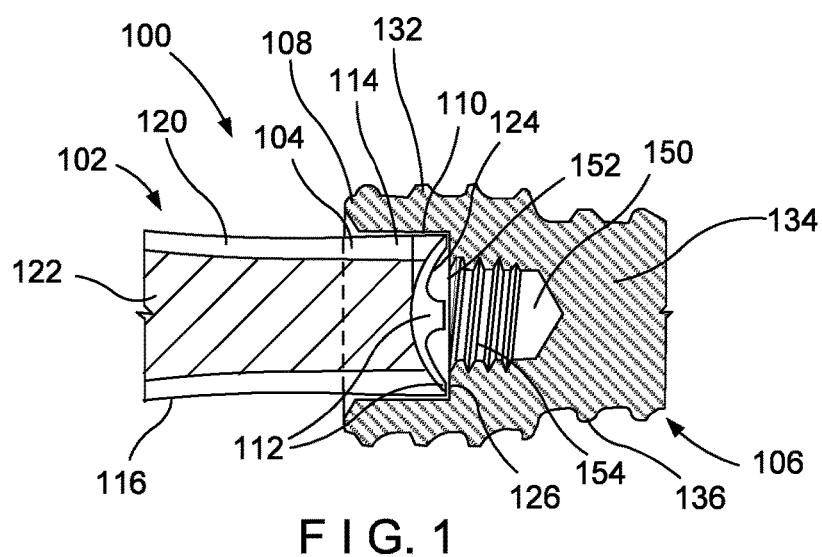
F I G. 1
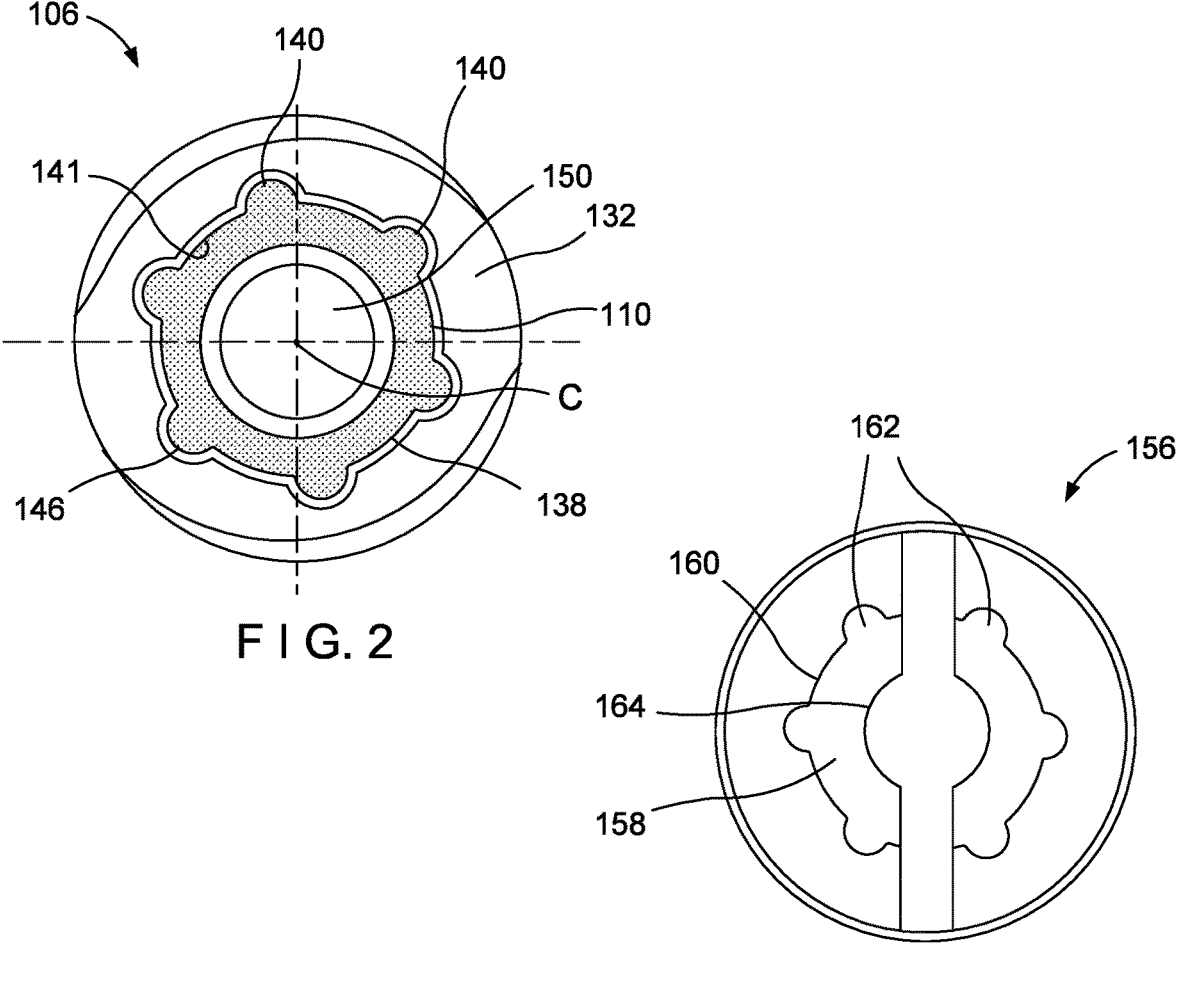
F I G. 2
F I G. 3

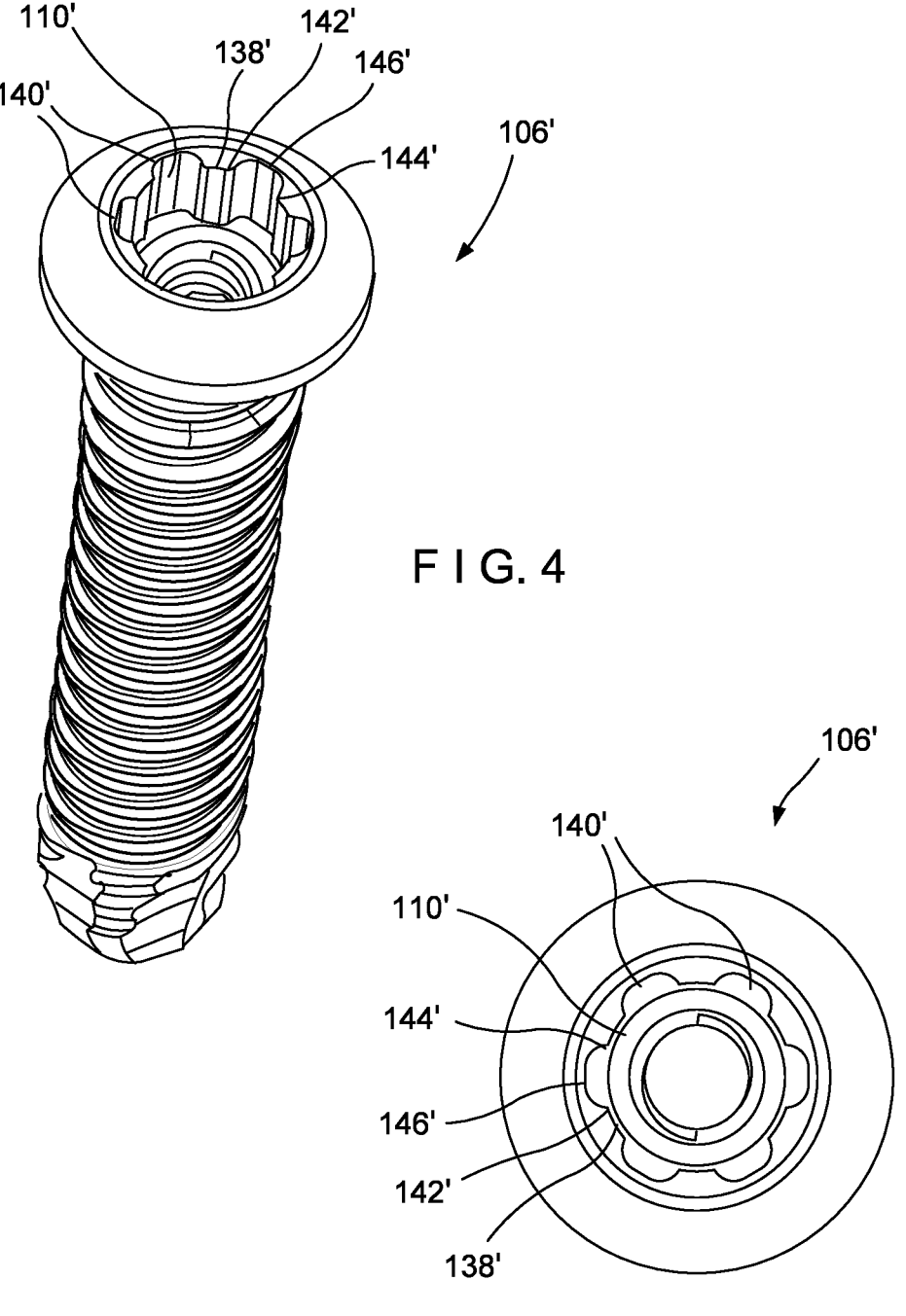
F I G. 4
F I G. 5

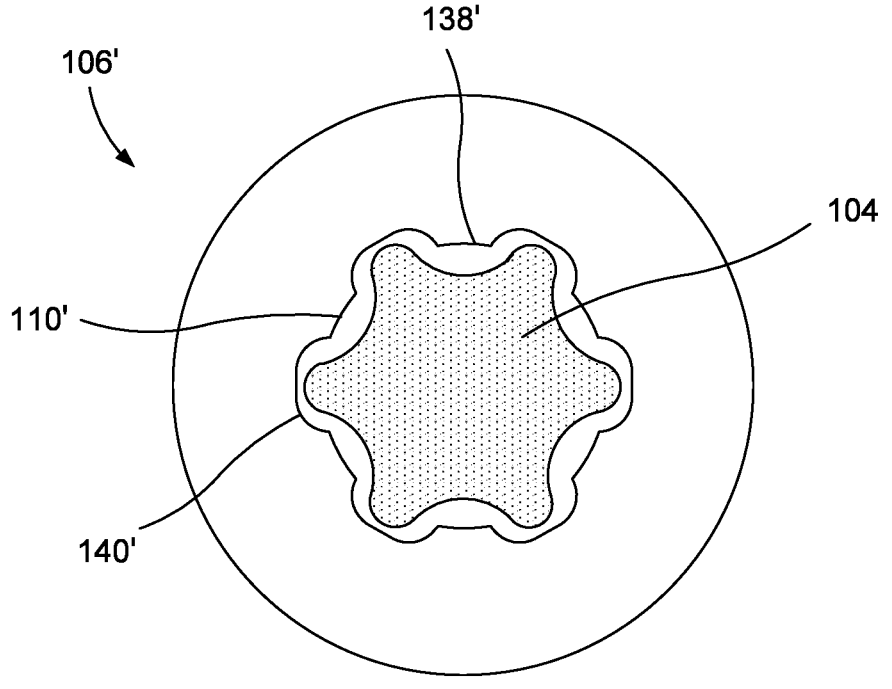
F I G. 6
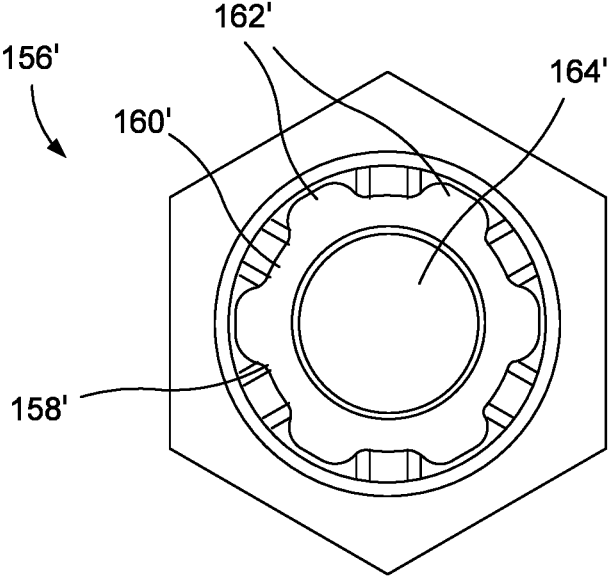
F I G. 7

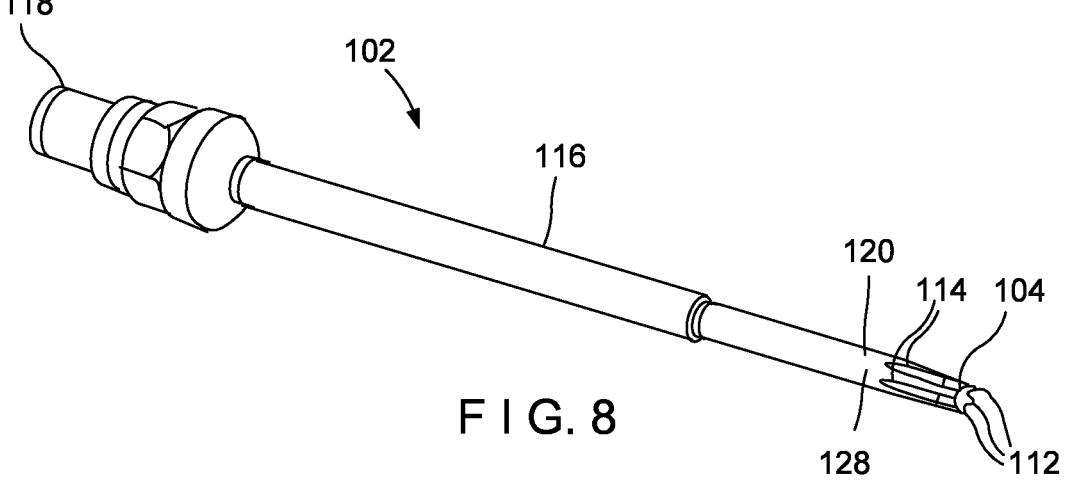
F I G. 8
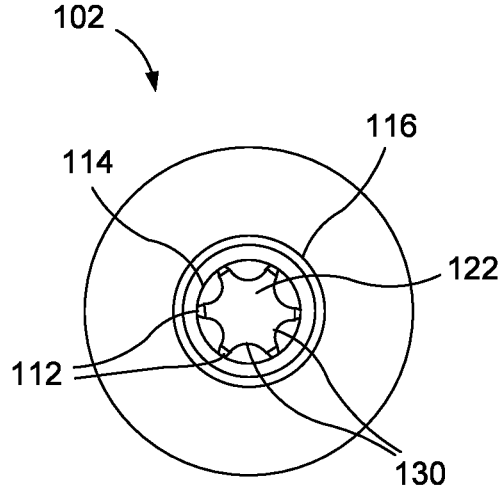
F I G. 9

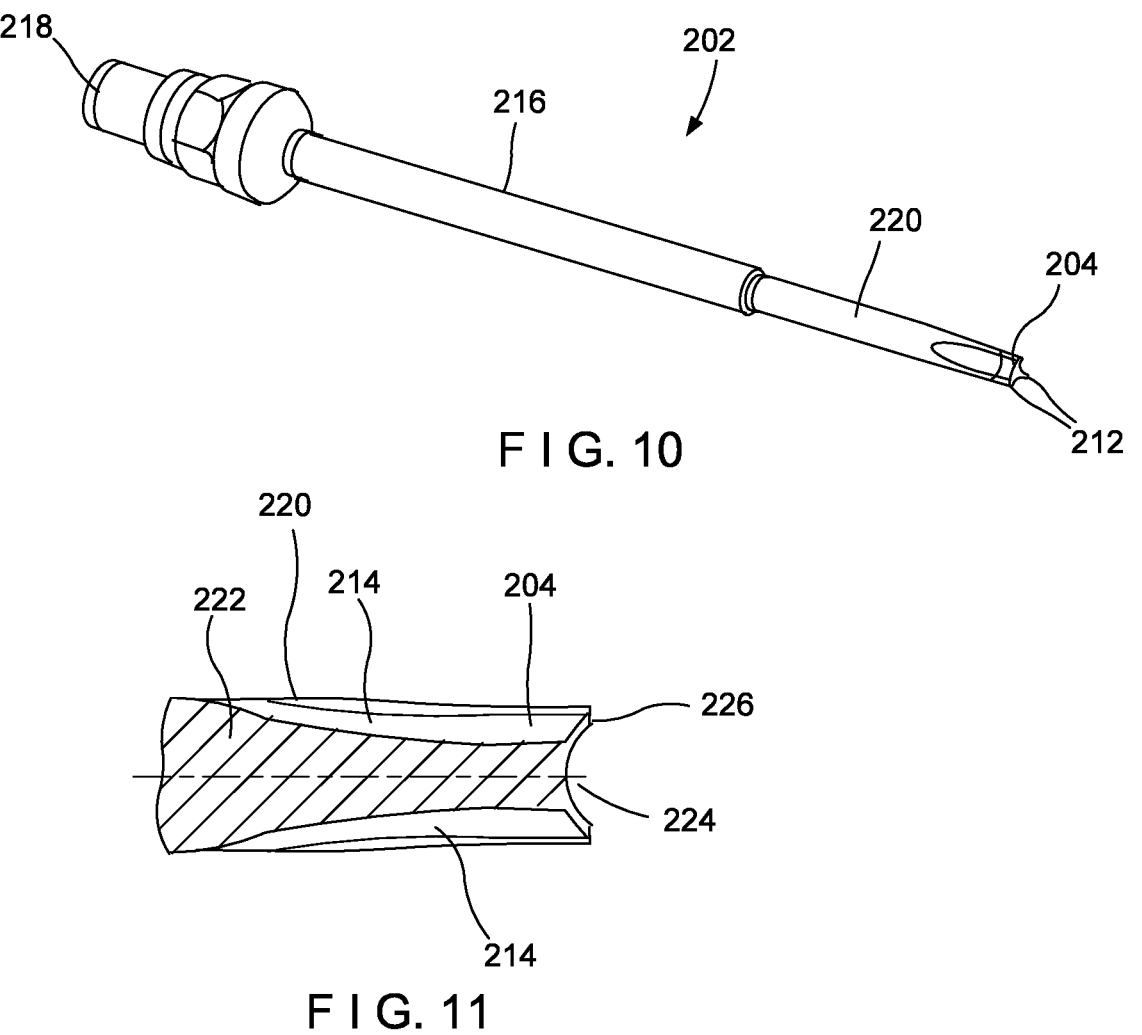
F I G. 10
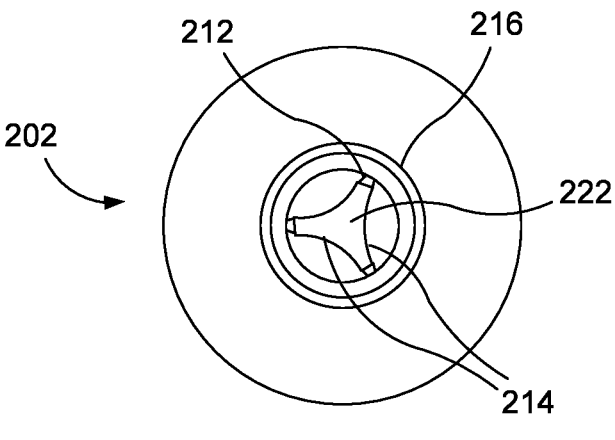
F I G. 11
F I G. 12

SCREW EXTRACTION SHAFT

PRIORITY CLAIM

This application is a Continuation Application of U.S. patent application Ser. No. 16/702,251 filed on Dec. 3, 2019, which has issued as U.S. Pat. No. 11,426,225. The disclosure of the above application is incorporated herein by reference.

BACKGROUND

Bone screws are often used to attach bone fixation devices such as, for example, intramedullary nails and/or bone plates, to a bone. In some cases, these bone screws must be removed from the bone after implantation. Bone screws are generally driven into and removed from a bone using a screwdriver including a distal end configured to engage, for example, a driving recess at a proximal end of the bone screw so that rotation of the screwdriver correspondingly rotates the bone screw. In some cases, however, tissue ingrowth over the driving recess makes it difficult for a conventional screwdriver to engage the bone screw to remove the bone screw from the bone.

SUMMARY

The present disclosure relates to a bone screw extraction device, comprising a shaft extending longitudinally from a proximal end to a distal tip, a distal portion of the shaft including a tissue-receiving cavity extending proximally thereinto from the distal tip, the distal tip including a plurality of fingers configured to be received within a driving recess of a bone screw and a plurality of channels extending longitudinally along an exterior surface of the distal portion, each of the plurality of channels extending between adjacent ones of the plurality of fingers.

The present disclosure also relates to a system for treating a bone, comprising a bone screw configured to be implanted into a bone, the bone screw extending from a proximal end to a distal end, the proximal end including a driving recess extending distally thereinto and an extraction device for removing the bone screw from a bone including a shaft extending longitudinally from a proximal end to a distal tip and, a distal portion of the shaft including a tissue-receiving cavity extending proximally thereinto from the distal tip, the distal tip including a plurality of fingers configured to be received within and engage corresponding portions of the driving recess of the bone screw and a plurality of channels extending longitudinally along an exterior surface of the distal portion, the plurality of fingers defined via a plurality of grooves extending proximally into a distal face of the distal tip, and each of the plurality of channels extending between adjacent ones of the plurality of fingers so that, as the distal tip is inserted into the driving recess, any soft tissue within the driving recess flows thereout of through the grooves and along the channels.

BRIEF DESCRIPTION

FIG. 1 shows a longitudinal cross-sectional view of a system according to an exemplary embodiment of the present disclosure;

FIG. 2 shows a plan view of a proximal end of a bone screw according to the system of FIG. 1;

FIG. 3 shows a plan view of a distal end of a screwdriver configured to drive the bone screw of FIG. 2;

FIG. 4 shows a perspective view of a bone screw according to an alternate embodiment of the system of FIG. 1;

FIG. 5 shows a plan view of a proximal end of the bone screw of FIG. 4;

FIG. 6 shows a plan view of the proximal end of the bone screw of FIG. 4 engaged with an extraction device according to the system of FIG. 1;

FIG. 7 shows a plan view of a distal end of a screwdriver for driving the bone screw of FIG. 4;

FIG. 8 shows a perspective view of an extraction device according to the system of FIG. 1;

FIG. 9 shows a plan view of a distal end of the extraction device of FIG. 2;

FIG. 10 shows a perspective view of an extraction device according to another exemplary embodiment of the present disclosure;

FIG. 11 shows a longitudinal cross-sectional view of a distal portion of the extraction device according to FIG. 4; and FIG. 12 shows a plan view of a distal end of the extraction device according to FIG. 4.

DETAILED DESCRIPTION

The present disclosure may be understood with reference to the following description and the appended drawings, wherein like elements are referred to with the same reference numerals. The present embodiments relate to the treatment of bone and, in particular, relates to a screw extraction device for removing a bone screw from a bone after implantation thereof. Exemplary embodiments describe an extraction device having a distal tip including a plurality of fingers sized and shaped to be inserted into a correspondingly sized and shaped driving recess of a bone screw along with a plurality of channels extending along an exterior surface of the distal tip between adjacent fingers so that, when the distal tip is inserted into the driving recess, in-grown material may flow between the fingers and along the channels to facilitate engagement of the distal tip with the driving recess to allow for removal of the bone screw. It will be understood by those of skill in the art that although the exemplary embodiments may be shown and described with respect to locking bone screws for an intramedullary nail, the screwdriver system of the present disclosure may be utilized for engaging and extracting any of a variety of bone screws in any of a number of different types of bone fixation systems. It should be noted that the terms proximal and distal, as used herein, are intended to refer to a direction toward (proximal) and away from (distal), respectively, a user of the device.

As shown in FIGS. 1-9, an extraction system 100 comprises an extraction device 102 including a distal tip 104 configured to engage a correspondingly sized and shaped driving recess 110 at a proximal end 108 of a bone screw 106. The distal tip 104 includes a plurality of fingers 112 (similar to the flutes of a column) separated circumferentially from one another by a plurality of channels 114 extending longitudinally from a distal end of the distal tip 104 along a portion of the length of a distal portion of an exterior surface 128 of the distal tip 104 so that, as the distal tip 104 is inserted into the driving recess 110 of a previously implanted bone screw 106, tissue that has grown into the driving recess 110 moves or flows between the fingers 112 proximally along the channels 114 to permit the distal tip 104 to be seated within the driving recess 108 while minimizing the force required. As will be understood by those of skill in the art, once the distal tip 104 is received within and engaged with the driving recess 110, the extraction device 102 may be rotated about a longitudinal axis thereof to extract the bone screw 106 from the bone.

The bone screw 106 may take any of a variety of configurations so long as the bone screw 106 includes a head portion 132 and a shaft 134 including a threading 136 extending therealong so that the bone screw 106 may be driven into and engaged a bone. The driving recess 110 extends into the head portion 132, at the proximal end 108 of the bone screw 106, and is engageable with one of a driving device (e.g., screwdriver) and/or an extraction device such as, for example, the driving device and the extraction device 102, to be driven into and/or extracted from the bone, respectively. In particular, when a driving and/or extraction device is engaged with the driving recess 110, a rotation of the driving/extraction device correspondingly rotates the bone screw 106 to drive the bone screw 106 into or remove the bone screw 106 from the bone.

In one embodiment, as shown in FIG. 2, the driving recess 110 includes a substantially circular central portion 138 along with a plurality of notches 140 formed along a surface 141 of the substantially circular central portion 138 so that the notches 140 extend radially outward from a longitudinal axis of the bone screw 106. In one embodiment, the driving recess 110 includes six notches 140, each of which are equally spaced from one another so that central axes of each of the notches 140, extends through a center point C of the substantially circular portion 138 and a center of each of the notches 140, extend at 60 degree angles relative to one another. An inner diameter—i.e., a diameter of the circular portion 138 of the driving recess 110—may range from between approximately 3.7 mm and 3.8 mm and, in one particular embodiment, may have an inner diameter of approximately 3.755 mm. Each notch 140 may be substantially semi-circular and sized so that an outer diameter—i.e., a distance from a radially outermost edge 146 of one of the notches 140 to a radially outermost edge 146 of a diametrically opposing one of the notches 140—ranges from between approximately 4.40 mm to 4.45 mm. A diameter of each of the semi-circular notches 140 may range from between 0.1 mm and 0.2 mm.

In one embodiment, the bone screw 106 further includes a retaining recess 150 extending distally from a distal end 152 of the driving recess 110 and including a retaining structure such as, for example, threading 154. In this embodiment, the threading 154 is configured to engage a retaining portion of a driving device so that the bone screw 106 is prevented from inadvertently disengaging from the driving device as the bone screw 106 is being driven into the bone. The retaining recess 150 may have a smaller diameter than the driving recess 110. According to one example, the retaining recess 150 has a diameter of 2.0 mm.

The bone screw 106 may be driven into the bone using, for example, a screwdriver 156 having a distal tip 158 corresponding in size and shape to the driving recess 110, as shown in FIG. 3. In particular, the tip 158 of this embodiment includes a substantially circular portion 160 and a plurality of protrusions 162 extending radially outward therefrom. In one embodiment, the distal tip 158 has six protrusions 162, each protrusion having a substantially semi-circular cross-section so that the distal tip 158 is specifically sized and shaped to be received within the driving recess 110. The screwdriver of this embodiment also includes a channel 164 extending therethrough to accommodate a retaining element of the screwdriver. In use, the retaining pin is inserted into the channel 164 so that a distal end thereof extends distally from the distal tip 158 to engage the retaining recess 150.

Although the exemplary embodiment described above provides specific values for the inner and outer diameters of the driving recess 110, along with a specific configuration of the notches 140, it will be understood by those of skill in the art that the inner and outer diameters of the driving recess 110 and the configuration of the notches 140 may be varied to increase or decrease a strength of engagement with the driving device, as desired. For example, in another embodiment, as shown in FIGS. 4-6, a driving recess 110' of a bone screw 106' may similarly include a substantially circular portion 138' and a plurality of notches 140' extending radially outward therefrom. In this embodiment, the driving recess 110' similarly includes six notches 140' which are equally spaced from one another. Rather than having a semi-circular shape, however, each of the notches 140' extends over a wider angle so that, for example, each notch extends over a symmetric angle of approximately 12 degrees. The angle over which each notch 140' extends may be defined via a first axis extending between a center point C of the driving recess 110 and a first end 142' of the notch 140' and a second axis extending between the center point C and a second end 144' of the notch 140'.

In addition, an inner diameter of the circular portion 138' of the driving recess 110' may be reduced relative to the inner diameter of the circular portion 138 of the driving recess 110 while the outer diameter defined via radially outermost edges 146' of the notches 140' is increased relative to the driving recess 110 to increase a contact surface of the driving recess with a driving device, thereby reducing a torsion resistance. For example, the inner diameter of the substantially circular portion 138' may, in one embodiment, range from between approximately 3.80 and 3.85 mm while the outer diameter defined via the radially outermost edges 146' of the notches 140' may range from between 4.5 mm to 4.8 mm. An increase in the width of each of the notches 140' (defined via a distance between the first end 142' of the notch 140' and the second end 144' of the notch 140') and a depth of each notch 140' (distance between the inner and outer diameters) relative to the notch 140 of the driving recess 110 may, in some cases, allow more ingrown tissue to be removed therefrom if the bone screw 106' requires subsequent removal.

As shown in FIG. 7, a screwdriver 156' for driving the bone screw 106' including the driving recess 110' according to an embodiment includes a distal tip 158' sized and shaped to correspond to the driving recess 110'. The distal tip 158' includes a substantially circular portion 160' and a plurality of protrusions 162' extending radially therefrom, the circular portion 160' and the protrusions 162' being sized to be received within the circular portion 138' and the notches 140' of the driving recess 110'. In particular, the circular portion 160' may have a smaller diameter than the circular portion 160 of the distal tip 158 and the protrusions 162' extend over a wider angle than the protrusions 162 of the distal tip 158 so that the distal tip 158' is sized to be received within the driving recess 110'. Similarly to the screwdriver 156, the screwdriver 156' may also include a channel 164' to accommodate a retaining element therein.

Although the above exemplary embodiments describe specific configurations of the driving recesses 110, 110', it will be understood by those of skill in the art that the driving recess (and the distal tips 158, 158' of the corresponding driving devices) may have any of a number of configurations. The central portion of the driving recess may have any of a variety of shapes from which the plurality of notches extends. Similarly, the driving recess may have any number of notches having any of a variety of shapes and sizes.

Self-retaining bone screws such as, for example, bone screws 106 are preferably milled during manufacturing to achieve the targeted performance. To reduce the cost of manufacturing and thus, the overall cost of the bone screws 106, portions of the driving recess 110 may be milled using existing milling machines such as, for example, milling machines for a standard M2.5 screw. Upon formation of a blank screw including a desired configuration of notches 140, a substantially circular central portion 138 and retention portion 150 including threading 154 may be milled using existing milling machines according to desired dimensions, as described above. Although milling of a bone screw is described with respect to the bone screw 106, it will be understood by those of skill in the art that the same manufacturing process including current milling machines for standard screws, may be used for milling portions of the driving recess 110' of the bone screw 106'.

The extraction device 102 may be used to extract a previously implanted bone screw such as, for example, the bone screw 106 (or the bone screw 106'). As described above, in some cases, tissue ingrowth within the driving recess 110 of the bone screw 106 makes it difficult to extract the bone screw 106 using a screwdriver in which the distal tip corresponds in size and shape to the driving recess 110. As shown in FIGS. 8-9, the extraction device 102 includes a longitudinally extending shaft 116 extending from a proximal end 118 to the distal tip 104, which is configured to be received within the driving recess 110 at the proximal end 108 of the bone screw 106. In one embodiment, the proximal end 118 includes a handle portion configured to facilitate gripping thereof via a user (e.g., surgeon) so that the extraction device 102 may be manually rotated to extract the bone screw 106. In another embodiment, the proximal end 118 is configured for attachment to, for example, a hand drill configured to electronically rotate the extraction device 102 to extract the bone screw 106.

A distal portion of the shaft 116 includes a tissue-receiving cavity 122 extending proximally into the shaft 116 from the distal tip 104 radially within the outer surface of the shaft 116 on which are formed the fingers 112. That is, the distal portion of the shaft 116 is hollowed out to form the tissue-receiving cavity radially within the distal tip 104 so that, as the distal tip of the shaft 116 is inserted into the driving recess 110 a first portion of in-grown tissue flows out of the driving recess 110 along the outside of the shaft 116 through the channels 114 while a second portion of the in-grown tissue is moved into the cavity 122. This permits the distal tip of the shaft 116 to be inserted into the driving recess 110 with a minimum of disturbance to the tissue surrounding the bone screw 106.

The fingers 112 are defined via grooves 124 extending proximally into a distal face 126 of the distal tip 104 to form a space between adjacent fingers 112. The distal portion 120 of the shaft 116 further includes the plurality of channels 114 extending along a portion of the length of the exterior surface 128 of the distal portion 120, proximally from the distal tip 104 so that each of the channels 114 extends between adjacent fingers 112 to further define the fingers 112. For example, each of the channels 114 may extend longitudinally along the distal portion 120 between distal-most tips of adjacent ones of the fingers 112. In one embodiment, the channels 114 extend into the tissue-receiving cavity 122 to define a cross-sectional shape of the tissue-receiving cavity 122. In other words, the channels 114 are defined via a wall of the distal portion 120 of the shaft 116.

The channels 114 and the grooves 124 define the fingers 112 so that each of the fingers 112 is specifically sized and shaped to be received within and engage a corresponding portion of the driving recess 110 of the bone screw 106. As shown in FIG. 1, each of the fingers 112 of the extraction device 102 are receivable within a corresponding one of the notches 140 to engage the driving recess 110 (or the driving recess 110', as shown in FIG. 7). Thus, when the fingers 112 are received within the notches of the driving recess 110, the distal tip 104 engages the driving recess 110 so that a rotation of the extraction device 102 about the longitudinal axis correspondingly rotates the bone screw 106 to remove the bone screw 106 from the bone.

As the distal tip 104 is inserted into the driving recess 110, in-grown soft tissue within the driving recess 110 is received within the tissue-receiving cavity 122 and/or flows between the fingers 112 along the channels 114 to facilitate insertion of the distal tip 104 into the driving recess 110. The channels 114 are configured such that, when the distal tip 104 is inserted into the driving recess 110, a gap or space exists between an exterior surface 130 of each of the channels 114 and a portion of an interior surface of the driving recess 110, along which a notch 140 does not extend, so that there is sufficient space along the exterior surface 128 of the distal portion 120 for the soft tissue to be pushed out of the driving recess 110. Thus, as the distal tip 104 is inserted into the driving recess 110, the soft tissue in-grown within the driving recess is 110 is pushed into the tissue-receiving cavity 122 and/or through the grooves 124 (i.e., between fingers 112) and along the channels 114 to permit engagement of the fingers 112 with the notches of the driving recess 110.

In one embodiment, the grooves 124 are equally spaced from one another circumferentially about the distal tip 114 so that the fingers 112 are equally spaced about a perimeter of the distal tip 104. In one example, the grooves 124 are arcuately shaped. It will be understood by those of skill in the art, however, that the distal tip 104 may include any shape or configuration of grooves 124 so long as the fingers 112 are sized, shaped and configured to correspond to the configuration of the driving recess 110 of the bone screw 106 that is to be removed from the bone. In addition, although the tissue-receiving cavity 122 is shown and described as extending longitudinally through only a distal portion 120 of the shaft 116, it will be understood by those of skill in the art that, in another embodiment, the tissue-receiving cavity 122 may extend through a longer portion of the length of the shaft 116 or even through the entire length of the shaft 116.

In one embodiment, a number of fingers 112 of the distal tip 104 corresponds to a number of notches within the driving recess 110. For example, as shown in FIGS. 1-4, the distal tip 104 includes six fingers 112 corresponding to the six notches of the driving recess 110. It will be understood by those of skill in the art, however, that the distal tip 104 may include any number fingers 112 in any of a number of configurations so long as the fingers 112 are configured to be non-rotatably received within and engaged with corresponding notches of the driving recess 110. In one embodiment, a length of the fingers 112 (e.g., a distance by which the grooves 124 extend proximally into the distal face 126) is less than a depth of the driving recess 110 (e.g., a distance from a proximal-most end of the groove to a distal end of the driving recess 110) to ensure sufficient engagement of the distal tip 104 with the driving recess 110 so that, when the extraction device 102 is rotated, sufficient torsional force is exerted on the bone screw to rotate and extract the bone screw 106.

Although the extraction device 102 is specifically shown and described as being configured to extract bone screws having driving recesses 110, 110', it will be understood by those of skill in the art that the extraction device 102 may be similarly used to extract any of a variety of bone screws having any of a variety of different driving recess configurations so long as the driving recess includes a plurality notches within which the fingers 112 of the extraction device may be received.

As shown in FIGS. 10-12, an extraction device 202 according to another exemplary embodiment of the present disclosure is substantially similar to the extraction device 102 described above with respect to the system 100 except as discuss. In particular, the extraction device 202 includes a shaft 216 extending from a proximal end 218 to a distal tip 204 and including a tissue-receiving cavity 222 extending through at least distal portion 220 thereof. Similarly to the extraction device 102, the distal tip 204 includes a plurality of fingers 212 defined via a plurality of grooves 224 extending proximally into a distal face 226 of the shaft 216 and spaced from one another circumferentially around the shaft 216.

The distal portion 220 also includes a plurality of channels 214 extending therealong, each of the channels 214 extending along the distal portion between adjacent fingers 212. Thus, as the distal tip 204 is inserted into a driving recess of a bone screw (e.g., the bone screw 106 as described above with respect to the system 100), in-grown soft tissue within the driving recess is pushed into the tissue-receiving cavity and/or through the grooves 224 and along the channels 214, to facilitate insertion of the distal tip 204 into the driving recess. As described above, a bone screw may include a plurality of radially outwardly extending notches within the driving recess for engaging the plurality of fingers 212 of the extraction device 202. Rather than having a number of fingers 212 corresponding to a specific number of radially extending notches within the driving recess, however, the fingers 212 of the extraction device 202 may be configured to occupy only some of the notches of the driving recess.

In one embodiment, the extraction device 202 includes a number of fingers 212 corresponding to half of the number of notches of the driving recess of the bone screw so that, each of the fingers 212 is insertable into an alternating one of the notches of the driving recess. For example, where the driving recess of the bone screw includes six notches, the distal tip 204 of the extraction device 202 includes three fingers 202, the fingers 212 configured about a perimeter of the distal face 226 so that the fingers 212 are inserted into every other one of the notches. The fingers 212 of this embodiment are spaced equidistantly from one another about the circumference of the shaft 216. It will be understood by those of skill in the art, however, that the distal tip 204 may include any number of fingers 212 and/or grooves 224 in any desired spacing so long as the fingers 212 are configured to be received within and engaged with the notches of the driving recess in a manner that facilitates extraction of the bone screw.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that they come within the scope of the appended claims and their equivalents.

What is claimed is:

1. A bone screw extraction device, comprising:
a shaft extending longitudinally from a proximal end to a distal tip, a distal portion of the shaft including a tissue-receiving cavity extending proximally thereinto from the distal tip, the distal tip including a plurality of fingers configured to be received within a driving recess of a bone screw and a plurality of channels extending longitudinally along an exterior surface of the distal portion, each of the plurality of channels extending between adjacent ones of the plurality of fingers,
wherein the distal tip is sized and shaped relative to the driving recess of the bone screw which the device is configured to extract so that, when the distal tip is inserted into the driving recess, a gap exists between an exterior surface of each of the plurality of channels and a radially adjacent surface of a central portion of the driving recess, with each of the plurality of channels being configured to cause, as the distal tip is inserted into the driving recess of the bone screw, any soft tissue within the driving recess to flow along the plurality of channels.

2. The device of claim 1, wherein the plurality of fingers is defined via a plurality of grooves extending proximally into a distal face of the distal tip.

3. The device of claim 1, wherein each of the plurality of channels extends along the distal portion from between distal-most tips of the adjacent ones of the plurality of fingers to further define a shape of the fingers.

4. The device of claim 1, wherein the plurality of channels is defined in a wall of the distal portion of the shaft.

5. The device of claim 1, wherein the plurality of channels extends radially into the tissue-receiving cavity of the shaft so that a cross-sectional area of the distal portion thereof is defined by the plurality of channels.

6. The device of claim 1, wherein adjacent ones of the plurality of fingers are equidistantly spaced from one another.

7. The device of claim 1, wherein the device comprises grooves, wherein the grooves are substantially arcuately shaped.

8. The device of claim 1, wherein the plurality of fingers includes six fingers.

9. The device of claim 1, wherein the plurality of fingers includes three fingers.

* * * * *